United States Patent [19]
Yelvington

[11] Patent Number: 5,468,928
[45] Date of Patent: Nov. 21, 1995

[54] PORTABLE APPARATUS FOR DESTROYING SYRINGE-TYPE NEEDLES

[75] Inventor: Richard D. Yelvington, Jacksonville, Fla.

[73] Assignee: Inventive Services, Inc., Jacksonville Beach, Fla.

[21] Appl. No.: 219,767

[22] Filed: Mar. 29, 1994

Related U.S. Application Data

[63] Continuation-in-part of Ser. No. 75,670, Jun. 11, 1993.
[51] Int. Cl.$^6$ .................................................. B23K 11/22
[52] U.S. Cl. ............................................................. 219/68
[58] Field of Search ................................ 219/68; 110/250

[56] References Cited

U.S. PATENT DOCUMENTS

| | | | |
|---|---|---|---|
| 4,628,169 | 12/1986 | Ch'ing-Lung | 219/68 |
| 4,965,426 | 10/1990 | Colombo | 219/68 |
| 5,138,124 | 8/1992 | Kirk et al. | 219/68 |
| 5,166,488 | 11/1992 | Peppard | 219/68 |
| 5,245,935 | 9/1993 | Fukuda | 219/68 |
| 5,264,675 | 11/1993 | Butler | 219/68 |
| 5,282,428 | 2/1994 | Greville et al. | 110/250 |
| 5,300,752 | 4/1994 | Elmerick et al. | 219/68 |

*Primary Examiner*—Geoffrey S. Evans
*Attorney, Agent, or Firm*—Deveau, Colton & Marquis

[57] ABSTRACT

An apparatus for destroying or rendering safe the metal needle portion of a hypodermic needle syringe in which the needle is destroyed by electrical resistance heating. The apparatus includes two electrodes that are generally disc shaped that are mounted so that they are a predetermined distance away from each other in an overlapping manner. During operation, the metal needle portion forms a resistive load between the electrodes which causes the metal to be incinerated and which causes switching circuitry to turn on a fan for a predetermined period of time. The fan draws smoke and emissions produced by incineration through a filter module. The filter module preferably includes a first filter having a porous layer and an antimicrobial layer, a second filter of activated carbon, a third filter of potassium manganate, and a fourth filter of activated carbon in series.

12 Claims, 8 Drawing Sheets

PORTABLE APPARATUS FOR DESTROYING SYRINGE-TYPE NEEDLES

RELATED APPLICATIONS

This application is a continuation-in-part of currently pending, application Ser. No. 08/075,670, which was filed on Jun. 11, 1993.

BACKGROUND OF THE INVENTION

1. Field of the Invention

This invention relates generally to the field of sterilizing and destroying the hypodermic needle component of a syringe so as to render it safe for disposal. This invention relates specifically to a portable apparatus which operates off of a rechargeable power source and which can operate while the power source is charging or when disconnected from the charging source. The invention incinerates and sterilizes the hypodermic needle component of the syringe by passing electricity continuously along portions of the needle component until significantly all of the needle portion has been burned due to the heat produced by the electrical resistance through the needle component, with the resistance heat also sterilizing any remaining portions of the needle component and the entry portal of the apparatus. The apparatus also comprises a fan which pulls air through a filter module causing any exhaust emission and pollutants to be filtered out by the filter module.

2. Prior Art

Current medical practice favors one-time use hypodermic needle syringes over reusable syringes. After a one-time use hypodermic needle syringe has been used, it must be disposed of properly. A used hypodermic needle syringe often poses a health hazard to any person coming into contact with a contaminated needle or syringe. The widespread exposure of contagious and fatal diseases multiplies this hazard.

The most common method for disposing of used hypodermic needle syringes is a "sharps'" container. A sharps' container merely is a plastic container into which the used hypodermic needle syringes are placed. When the container is full, a cap is placed on the container and the container is disposed of. Typically, a service picks up the full sharps' containers and disposes of the full containers either through incineration or in landfills. When destroyed in incinerators, the sharps+ container provides a sufficient method of disposal of the used hypodermic needle syringes. However, sharps' containers suffer from several disadvantages. First, the used hypodermic needle syringes are not sterilized before being placed in the sharps' container. This can lead to unintentional contact with a contaminated needle. Second, if the sharps' containers are disposed of in a landfill, there always is the possibility that the sharps' container can inadvertently open or be broken, thus exposing the contaminated needles.

An electrical syringe needle destroyer is disclosed in U.S. Pat. No. 4,628,269 to Ch'ing-Lung. The Ch'ing-Lung device comprises a pair of spaced apart electrodes within a self-contained unit. The needle of the syringe is inserted into an opening in the unit until the base of the needle component is positioned between the two electrodes. When electricity is passed between the electrodes, the electricity causes the portion of the needle between the electrodes to melt, thus severing the needle from the syringe body. The needle portion falls into a collection means and can be disposed. The Ch'ing-Lung device may not destroy the needle, but merely severs the needle from the syringe body. Therefore, the Ch'ing-Lung device does not eliminate the dangers of contamination from the end of the needle, nor the safety hazard obvious from the possibility of having many loose needle heads in the unit. Furthermore, the Ch'ing-Lung device requires two-handed operation. Also, the electrodes do not collapse toward each other which allows ½ to ¼" of the needle to remain after incineration.

A plastic syringe destruction device is disclosed in U.S. Pat. No. 4,860,958 to Yerman. The Yerman device employs a cylinder and piston compaction unit which uses heat to thermally smash complete plastic syringes, including the needle component, into a compacted mass. One or more plastic syringes are placed in the cylinder and the cylinder lid is closed. The syringes then are heated to temperatures between 100° C. and 200° C. to bring about melting of the syringes, as well as sterilization. The piston travels upwardly in the cylinder while the syringes are at temperature, thus compacting the softened or molten plastic syringes into the compacted mass. The Yerman device suffers from several disadvantages, the most important of which is that the syringes are not raised to a temperature high enough to destroy the metal needle portion of the syringe. After the plastic syringes have been compacted into a mass, the metal needles typically protrude from the plastic mass, thus still posing a danger to the operator. Although the needles may have been sterilized, puncture wounds caused by the needles are neither desired nor healthy.

A hypodermic syringe needle destroying and sterilizing apparatus and method is disclosed in U.S. Pat. No. 4,877,934 to Spinello. The Spinello device is aimed specifically at destroying the metal needle portion of the hypodermic syringe by using electrical resistance heating between electrodes. The hypodermic needle is placed in a carrier which contacts the upper portion of the metal needle closest to the syringe barrel. The carrier then carries the syringe over an upwardly sloping second electrode. As the needle point contacts the second electrode, electricity passes from the second electrode through the metal needle into the first electrode, thus causing resistance heating of the metal needle. In theory, the electrical resistance heating melts and destroys the metal needle. However, in practice, the electrical resistance heating may only soften the metal needle such that as the metal needle contacts the upwardly sloping second electrode, the metal needle bends outward. Although the Spinello device may heat the metal needle to a temperature high enough to sterilize it, typically the metal needle remains and poses the same health and safety hazard any other sharp instrument has. The Spinello device also comprises many moving parts which have the potential of jamming and wearing and no provisions are made for sterilizing the moving parts. Furthermore, this device operates along the full length of the needle which again leads to problems. If the needle has a crack in it or when the upper electrical grip holds the very top of the needle, it may break off causing an unburned part of the needle to fall into the particle tray. The needle destruction unit of the present invention burns off a section at a time, insuring the needle is destroyed and sterilized. Also there is not a provision in Spinello for filtering smoke and emissions as is provided by the present invention. The portal entry of the Spinello device has no provisions for being sterilized. Therefore, when the needle is placed in the device, whatever blood is on the needle may infect the portal entry area as well. In contrast, the present invention provides means for sterilizing the portal entry plate.

A disposable needle and syringe destructor unit is disclosed in U.S. Pat. No. 4,969,379 to Taylor, et al. The Taylor device essentially is a syringe guillotine. The syringe is inserted into a receiving hole a certain distance, and a spring-biased piston is hand actuated forcing a cutting member down on the syringe. The process is repeated until the entire syringe has been cut into smaller portions, which portions fall to the bottom of the container. Obviously, the Taylor device suffers from the disadvantage that the syringe is not sterilized and the metal needle portion, although in smaller pieces, still presents a safety hazard. After the Taylor device is full of syringe portions, it must be disposed of in much the same manner as the sharps' containers.

It appears that this device may violate the Federal Regulation Vol. 56, No. 235, Sect. 1910-1030, which prohibits shearing or breaking of contaminated needles. While rendering the syringe unusable, the blades become contaminated with whatever blood or foreign matter is on the needle or in the syringes themselves. Furthermore, shearing may cause an aerosol release of blood which is dangerous and therefore undesirable. Also, the Taylor device is a two handed device with which one hand must be used to press down on the chopper blade while the other hand holds the syringe. The needle destruction unit of the present invention can be operated with one hand. A user simply inserts a needle into the unit through the portal entry using only one hand and the needle is automatically incinerated.

One prior art device known as the Bacti-Cinerator III is a 120 volt plug-in flameless sterilizer model for inoculating loops, needles and culture tube mounts. The unit operates at 1500 degrees Fahrenheit, 815 degrees centigrade and has been on the market approximately ten years. It is accepted by the FDA as a safe way to sterilize needles. However, the Bacti-Cinerator does not contain a filtering system, so whatever biological elements are on the needles or inoculating loops are burned off and allowed to escape into the air. In contrast, the present invention provides that smoke and gases generated during incineration are filtered properly before being released into the room. Therefore, the present invention is generally safer and takes into account the FDA's concerns over emissions.

U.S. Pat. No. 4,565,311, dated January 1986 discloses a device for syringe disposal. This is a device for shearing needles and syringes. Parts from the sheared needles fall into a tray or container placed in the bottom of the machine. The machine is essentially a set of blades connected to a solenoid. A syringe is dropped down into an aperture where it falls into a cone shaped holding area. The blades then work back and forth against the needle and the syringe body chopping them into pieces. Disposal devices such as this may violate Federal Regulation Vol. 56, No. 235, Sect. 1910-1030 which states that contaminated needles and other contaminated sharps should not be bent, recapped or removed except as noted in Paragraphs D, 2, ViiA and D, 2, ViiB; shearing or breaking of contaminated needles is prohibited. When using this device, blood may be released as the needle or the syringe body is sheared. This would cause splattering inside the device which means that the blades would constantly be infected. There are no provisions made to sterilize the blades of this device. Therefore, the device may be an open source of contamination, particularly when the device would need repair. It may have to be decontaminated or steam cleaned prior to being worked on. While it destroys syringes by chopping them up into little pieces and rendering them unusable, the needles are still there, are still contaminated and still have the chance of sticking someone.

U.S. Pat. No. 4,628,169, dated Dec. 9, 1986 discloses an electrode needle destroyer. This device consists of a frame and cabinet with two electrodes, a transformer and a small tray for collecting needle fragments. This device uses electrodes to burn the needle off. However, it operates on burning the full length of the needle which requires more power than does the needle destruction unit of the present invention. The electrodes are very small and made of metal. The unit has a transformer plugged directly into a wall outlet so that as the needles are burned, it draws power through the transformer. This may cause a radio frequency signal that can interfere with the delicate equipment in operating rooms or a physician's office. This also reduces the portability of the device. Furthermore, there are no provisions in this device for removing smoke or emissions resulting from incineration. Also, the device is not practical because the electrodes may become coated with metal fragments and short out after a short number of uses.

U.S. Pat. No. 5,076,178, dated Dec. 31, 1991 discloses a device which heats and softens a syringe needle to sterilize it and then rolls the needle into a ball. This process leaves the needle intact although it is shaped into a spiral. The device relies on ultraviolet light and heat for sterilization. Tests have shown ultraviolet light to be efficient primarily on exposed surfaces but insufficient to deal with machine parts not directly under the beam. The device also crimps and shears the needle, which may also violate Federal Regulation No. 56, No. 235, Sect. 1910-1030. Also, the device requires 115 volts on a continuous basis and is not portable.

Therefore, it can be seen that there exists a need for an apparatus for sterilizing and destroying the metal needle component of a hypodermic needle syringe with a minimum of operator intervention and a minimum of moving or mechanical parts and which is in compliance with federal regulations. While past methods destroy a portion of the needle and may sterilize the needle, these devices do not do a complete job of destroying the entire needle component of the syringe, and the used hypodermic needle portion of the syringe is still not safe to the handler or for the environment. The present invention overcomes the disadvantages of the prior art by thoroughly burning and destroying significantly all of the needle portion of the syringe by continuously passing a sufficient amount of electricity through the needle, burning and destroying portions of the needle at a time. Any remaining needle portion, particularly the nub of the needle closest the syringe barrel, also has been heated, through electrical resistance heating, to a sufficient temperature for a sufficient period of time to sterilize any remaining needle portion. Unlike the prior art which acts upon only the base and tip of the needle, the present invention acts only on a small portion of the needle at a time, eliminating the need for the high amperages and voltages required by the prior art, and eliminating the problem of needles breaking between the base and tip and needles welding themselves to the electrodes as frequently occurs in the prior art devices. The present invention also prevents blood aerosol release and provides means for filtering out smoke and gases which may be produced during incineration.

One of the problems confronted by the present invention was to design electrodes that would not melt at temperatures needed for incineration (i.e., approximately 2800° F.). Some of the prior deneedling devices utilize electrodes which cause portions of the melted needles to be welded to the electrodes. The present invention solves this problem by using electrodes comprised of carbon. Although portions of the melted needle may lightly adhere to the surfaces of the electrodes, they immediately come off or are forced off when another syringe is placed in the unit as described in more detail below.

Another problem inherent in some of the prior deneedling devices is that they require relatively high current to operate. Due to the fact that the apparatus of the present invention burns only small portions of the needle at a time, power requirements are for less than devices designed to rely on electrodes positioned at the base and tip of the needle, or which are otherwise designed such that they require a relatively high current to incinerate a needle. The relatively low current requirement allows the present device to use a rechargeable current source, as described below, which allows the present device to incinerate a number of needles before needing recharging, and to be small enough so as to be portable.

In accordance with a preferred embodiment of the present invention, a 12 volt rechargeable power source is utilized. The power source can be charged from total discharge to full charge in approximately five hours on a standard 300 milliamp charger. The power source is preferably comprised of ten 1.2 volt ni-cad batteries arranged in series. The needle destruction unit runs off of 7.2 volts obtained by tapping six batteries of the series arrangement. The filtering means comprises a fan which runs off of 12 volts obtained by tapping all ten of the ni-cad batteries. The arrangement allows up to approximately 80 needles to be destroyed before recharging as described in detail below.

Some advantages of using a relatively low current to incinerate the needles are that radio frequency interference is avoided, sparking and aerosol release are avoided, and mobility is enhanced in that the apparatus need not include a large power source. Moreover, the apparatus of the present invention can be used while it is charging.

BRIEF SUMMARY OF THE INVENTION

The present invention provides an apparatus which destroys significantly all of the metal needle portion of the hypodermic needle syringe, and sterilizes remaining portions of the needle, particularly any hub of the metal needle remaining. The operator inserts the metal needle portion of the hypodermic needle syringe through an opening into the burner unit which comprises two electrodes. The electrodes are generally circular discs of high grade carbon and are spaced apart from each other, preferably one-eighth to three-sixteenths of an inch (⅛"–³⁄₁₆"), in an overlapping relationship relative to the opening, with one of the electrodes located proximal to the opening and one of the electrodes located distal to the opening. Each electrode is rotationally journaled on separate central shafts and secured to an independent lead having flexible, spring-like qualities. The spring leads hold the electrodes in their starting positions. Alternatively, each electrode is held in its desired starting positions using compression springs located on the central shaft between the electrode and the lead. As the needle is inserted through the opening, first the shaft of the needle contacts the circumferential edge of the first proximal electrode, then second, as the needle is inserted further through the opening, the tip of the needle contacts an upper surface portion of the second distal electrode.

One of the electrodes is connected to the positive terminal of a rechargeable DC power source and the other electrode is connected to the negative terminal of the DC power source, in the preferred embodiment. An electrical arc is created across the two electrodes. Since the two electrodes are spaced approximately one-eighth to three-sixteenths of an inch (⅛"–³⁄₁₆") apart in the preferred embodiment, the electrical arc only acts on this portion of the needle at a time, burning the tip off of the needle continuously as the tip contacts the distal electrode. As the needle is inserted into the opening, one-eighth to three-sixteenths of an inch (⅛"–³⁄₁₆") of the needle is subjected to the electrical arc at a time, thus eliminating the high amperage and high voltage power sources previously necessary to act on the entire needle length.

Once the needle has been inserted into the opening up to its base where it is attached to the syringe barrel, the base forces the proximal electrode downward in the direction of the distal electrode by causing the spring lead to flex downward, thus lessening the distance between the two electrodes and allowing the remaining portion of the needle to be subjected to electric current and burned off at the tip contacting the distal electrode. In the alternative embodiment the needle base forces the proximal electrode downward on its shaft in the direction of the distal electrode, compressing the first electrode shaft spring, thus lessening the distance between the two electrodes and allowing the remaining portion of the needle to be subjected to the electrical current and burned off at the tip contacting the distal electrode. Once the deneedled syringe is removed from the opening, the first electrode spring lead, or the shaft spring, returns the first electrode to its starting position.

The electrical current has the effect of incinerating the metal needle through resistance heating and/or arcing, thus destroying it. For any portion of the metal needle not incinerated, the electrical arc creates resistance heating of the metal needle to a temperature sufficient to sterilize the metal needle portion, namely greater than 100° C. Any melted portions of the metal needle are sterilized by the resistance heat and fall into a disposal unit or debris box.

The deneedled hypodermic needle syringe is then removed from the burner unit and can be destroyed using any conventional barrel destruction unit or, preferably, the barrel sterilization and compactor unit disclosed and claimed in the parent application hereto.

The filter means of the present invention preferably comprises a first filter which has a porous layer for filtering out larger particles such as soot and a second layer saturated with antimicrobial disinfectant to disinfect the particles, a second filter comprised of activated carbon for filtering out smoke, a third filter comprised of potassium manganate for filtering out odors, a fourth filter comprised of activated carbon for filtering out smoke, and a fan for pulling air through the filters. The present invention is housed in a casing which is shaped to generate a plenum when the fan is turned on. Upon commencement of incineration, the fan automatically turns on and begins pulling air from the front of the unit, through the unit, including by the electrodes, and through the filters. A timer controls the duration of time that the fan is on. Any exhaust emission and pollutants are absorbed by the filters and the air exhausted back into the room is odor free and particulate free.

Accordingly, it is an object of the present invention to provide an apparatus for destroying metal needles using electrical resistance heating.

Another object of the present invention is to provide an apparatus for destroying the needle component of a syringe by destroying and/or incinerating the metal needle component of the hypodermic syringe and sterilizing any remaining portion of the needle.

It is another object of the present invention to provide an apparatus for destroying needles which renders any unburned portions of the needle sterile and not harmful to the operator and other humans.

Still another object of the present invention is to provide a syringe needle destroyer which will meet US OSHA requirements and USEPA and hospital approval for a medical device which sterilizes and destroys used hypodermic syringe needles.

Yet another object of the present invention is to provide an apparatus for destroying needles which is a compact, stand alone unit which can be used by hospital wards, individual hospital rooms, doctors' examining rooms, dental or veterinary practices.

It is an object of the present invention to provide an apparatus for destroying needles which is simple and efficient in operation, durable in construction, and ecologically friendly.

Another object of the present invention is to provide an apparatus for destroying needles which uses a lower amperage and lower voltage power source when compared to current art devices, thus using less electricity and being more economical than current art devices, and preventing radio frequency interference.

Still another object of the present invention is to provide an apparatus for destroying needles which renders the entire used syringe safe for handling.

Yet another object of the present invention is to provide an apparatus for destroying needles in which significantly all of the needle is destroyed without the need for a great deal of operator manipulation, thus making the present invention more safe than current art devices.

It is yet another object of the present invention to provide an apparatus for destroying needles which comprises a filtering means for filtering out exhaust emissions and pollutants so that air exhausted from the apparatus is odor free and particulate free.

It is another object of the present invention to provide an apparatus for destroying needles which operates off of a rechargeable power source and which can be used while the power source is being charged or when disconnected from the charging source.

Further objects of the present invention are to provide an apparatus for destroying needles which minimizes portions of the metal needle from being welded to the electrodes, has a relatively low noise level, prevents sparking and aerosol release, and is portable and relatively light weight.

These objects, and other objects, features and advantages of the present invention, will become more apparent to one skilled in the art when the following detailed description of the preferred embodiment is read in conjunction with the appended figures in which like reference numerals denote like components throughout the several views.

BRIEF DESCRIPTION OF THE DRAWINGS

FIG. 12b is a front view of the electrodes shown in FIG. 12a.

DETAILED DESCRIPTION OF THE PREFERRED EMBODIMENT

Figure 1:
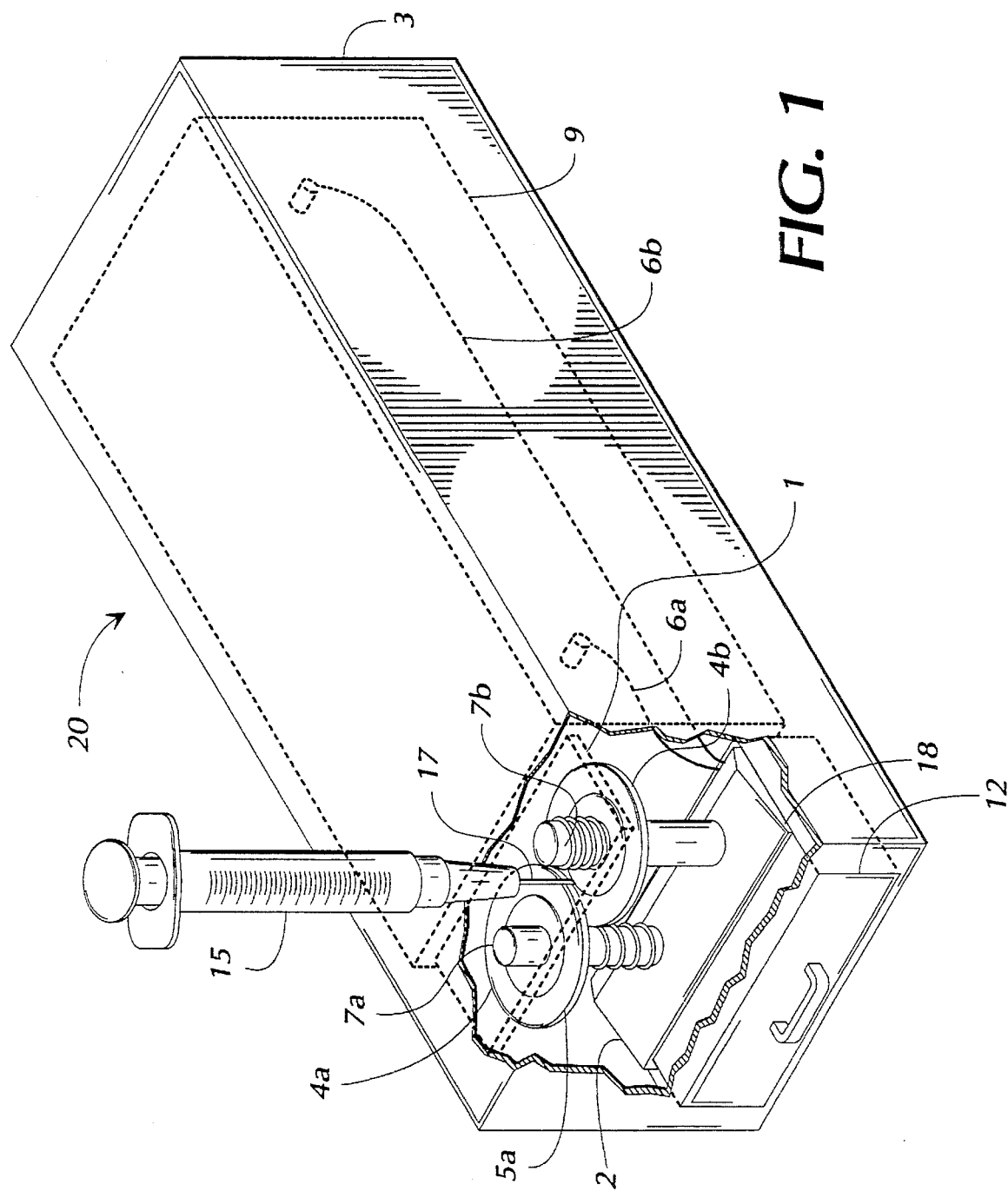
FIG. 1 is a perspective view of one embodiment of the needle destroyer unit of the present invention.

With reference now to the figures, one basic embodiment of the needle destruction unit 20 of the present invention will be described by first describing the various components and how they are structurally related to each other and then describing the sequence of operations for destroying a hypodermic syringe needle. The preferred embodiment then is described in structural detail and sequential operation.

This embodiment of the needle destruction unit 20 comprises a relatively small housing 3, generally approximately the size of an electric pencil sharpener assembly, that allows the needle 17 of one syringe 15 at a time to be destroyed. The housing 3 is a generally rectangular cubic hollow structure which contains the needle destroying means, the refuse collection means, and the power means. Housing 3 has a front wall through which a needle debris box 12 may be accessed, a top wall through which an opening 16 is formed providing needle 17 access to the interior of the unit, left, right and back walls relative to the front wall, and a bottom wall.

The needle destroying means comprises two overlapping disc electrodes 4 preferably comprised of high grade carbon. The electrodes 4 may be comprised of any suitable electrode material; however, high grade carbon provides the preferred electrical conduction level, has a satisfactory lifetime and helps to prevent welding of needle material onto the electrodes 4. The electrodes 4 are generally disc-like in structure, having an upper surface, a lower surface, a circumferential surface, and a central, axial hole. The upper surface and lower surface of upper or proximal electrode 4a taper toward each other in the direction from the center of the proximal electrode 4a out to the circumferential surface of proximal electrode 4a. The upper surface of lower or distal electrode 4b tapers downward toward the lower surface of distal electrode 4a in the direction from the center of the distal electrode 4b out to the circumferential surface of distal electrode 4b.

In this embodiment, each of the electrodes 4 are rotationally and slidably mounted horizontally on vertical standoffs or shafts 7, each electrode 4 being able to slide upwardly or downwardly on its respective shaft 7. Being horizontally mounted on vertical shafts 7, the upper surfaces of the electrodes 4 taper in a downward direction from the centers to the circumferential surfaces of the electrodes 4, the lower surface of proximal electrode 4a tapers in an upward direction from the center to the circumferential surface of proximal electrode 4a, and the lower surface of distal electrode 4b is horizontal.

Shafts 7 are journaled at their upper ends in a first ceramic support structure 1, and at their lower ends in a second ceramic support structure 18. First ceramic support structure 1 is a generally rectangular cubic structure horizontally mounted on the interior surface of the top wall of housing 3. Second ceramic support structure 18 also is a generally rectangular cubic structure mounted at one end to the left wall of housing 3 and at the other end to the right wall of housing 3 such that second ceramic support structure 18 is located directly below first ceramic support structure 1 approximately midway between the top wall and the bottom wall of housing 3.

Located immediately above second ceramic support structure 18 is deflector insulator 2 constructed of an electrically non-conducting material. Deflector insulator 2 has a generally triangular structure much like the roof of a typical house or a ridge. Deflector insulator 2 also is mounted at one end on the left wall of housing 3 and on the other end on right wall of housing 3 and has generally the same horizontal dimensions as second ceramic support structure 18. Deflector insulator has two pass-through holes located along the apex of the structure. As described in more detail below, shafts 7 pass through these two pass-through holes.

Copper pads 11 are mounted on second ceramic support structure 18. Shafts 7 extend downwardly from first ceramic support structure 1 through the pass-through holes in deflector insulator 2, and terminate abutting copper pads 11. Copper pads 11 must not touch each other so that they are electrically insulated from each other on second ceramic support structure 18. Shafts 7 also must be constructed of an electrical conducting material. In this manner, proximal electrode 4a, mounted on shaft 7a which abuts copper pad 11a is electrically insulated from distal electrode 4b which is mounted on shaft 7b, which abuts copper pad 11b.

Helical compression springs 14 are mounted on shafts 7 such that shafts 7 pass through the center of the helix of helical compression springs 14. Spring 14a is mounted on shaft 7a below proximal electrode 4a such that spring 14a is located between proximal electrode 4a and deflector insulator 2. Compression spring 4b is mounted on shaft 7b above distal electrode 4b such that it is located between first ceramic support structure 1 and distal electrode 4b. In this manner, proximal electrode 4a is maintained in a position generally abutting first ceramic support structure 1 by compression spring 4a, and distal electrode 4b is maintained in a position generally abutting deflector insulator 2 by compression spring 4b. Flat washer 13 may be located between distal electrode 4b and deflector insulator 2 as a spacer and to allow freer rotation of distal electrode 4b about shaft 7b. A flat washer 13 also may be located between proximal electrode 4a and first ceramic support structure 1 also to act as a spacer and to allow freer rotation of proximal electrode 4a about shaft 7a.

Figure 4:
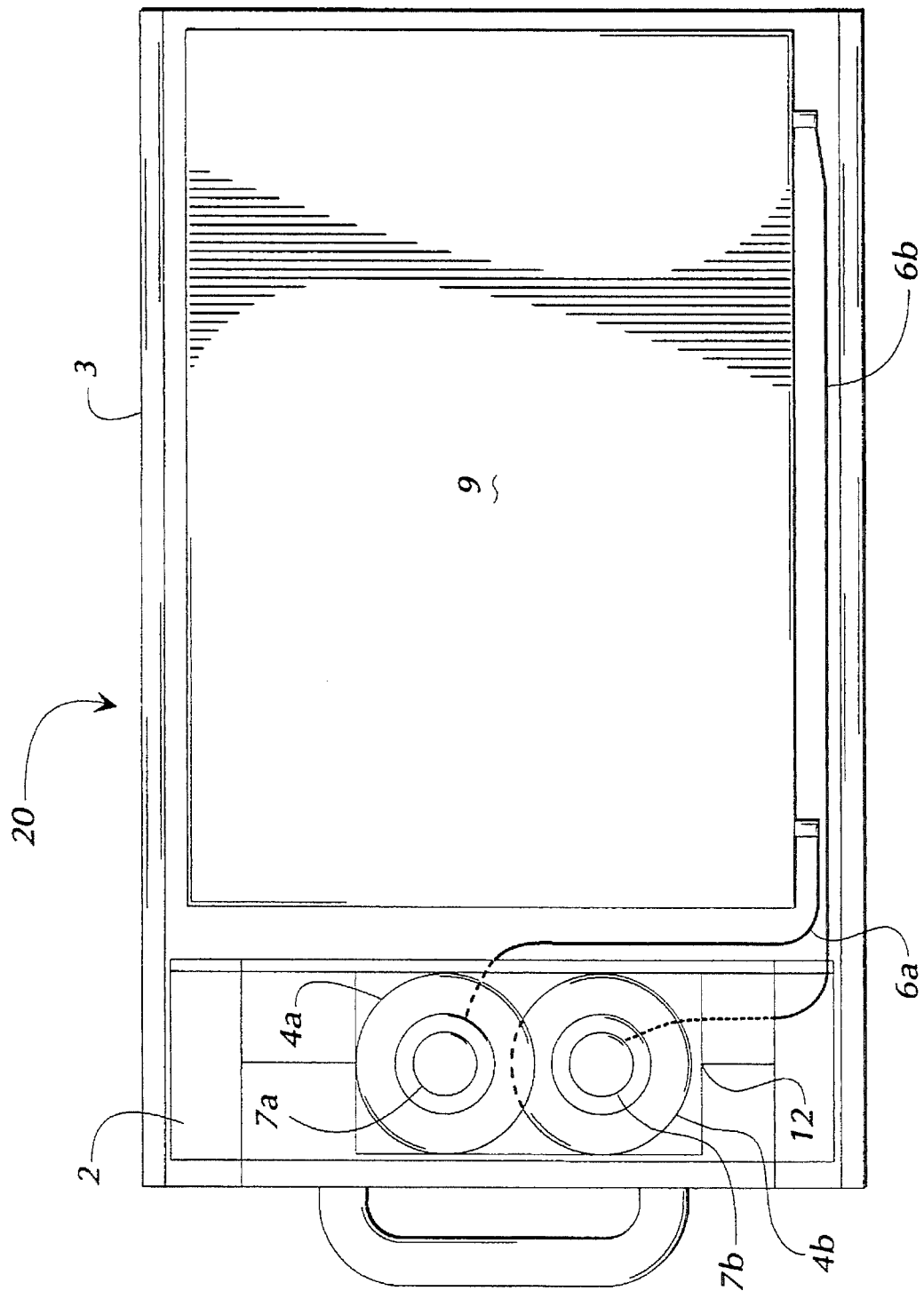
FIG. 4 is a top view, partly in section, of the needle destroyer unit as in FIG. 1.

In the starting and operating position for this embodiment, compression spring 14a threes proximal electrode 4a upwardly against first ceramic support substrate 1 or flat washer 13, if present, and second compression spring 14b forces distal electrode 4b downwardly against deflector insulator 2 or flat washer 13, if present, thus creating a gap of up to one-half inch (½"), and preferably between approximately one-eighth of an inch and three-sixteenths of an inch (⅛"–³⁄₁₆"), between the lower surface of proximal electrode 4a and the upper surface of distal electrode 4b. As can be seen in greatest detail in FIG. 2a, FIG. 2b and FIG. 4, electrodes 4 overlap each other by a predetermined distance. Needle access opening 16 is located generally above this overlap. Opening 16 extends through the top wall of housing 3 and first ceramic support substrate 1 and is generally circular in shape, and has a diameter slightly larger than the diameter of the typical hypodermic syringe 15. Opening 16 is positioned above the overlap of the electrodes 4 such that when the hypodermic syringe 15 is inserted into the opening 16, as discussed in more detail below, the shaft of the needle 17 of the hypodermic syringe 15 abuts the circumferential surface of proximal electrode 4a and the tip of the needle 17 contacts the upper surface of distal electrode 4b.

Located immediately below the electrodes 4, deflector insulator 2, and second ceramic support substrate 18, is needle debris box 12. Debris box 12 is a drawer-shaped rectangularly cubic component having a bottom wall and four upstanding side walls. Debris box 12 can be accessed from the front wall of housing 3 by sliding the box inward and outward of housing 3. As shown in greatest detail in FIG. 3 and FIG. 4, debris box 12 has a front to back dimension somewhat greater than the front to back dimension of deflector insulator 2 such that any matter falling on the downwardly sloping upper surface of deflector insulator 2 will slide off and will accumulate in debris box 12. As more fully discussed below, needle ash and other debris created during the destruction of the needle 17 falls onto the downwardly sloping upper surface of deflector insulator 2 and falls by gravity into debris box 12.

Located in the rearward portion of housing 3 is battery 9. Battery 9 can be any direct current electrical power source including, but not limited to, disposal batteries, rechargeable batteries, or an alternating current to direct current transformer. The negative terminal of battery 9 is electrically connected to copper pad 11a via lead wire 6a. Likewise, the positive terminal of battery 9 is electrically connected to copper pad 11b via lead wire 6b. As electrodes 4 are in electrical contact with shafts 7 and shafts 7 are in electrical contact with copper pads 11, and electrodes 4, shafts 7, and copper pads 11 are electrical conductors, direct electric current paths are created between the negative terminal of battery 9 and proximal electrode 4a through lead wire 6a, copper pad 11a, and shaft 7a, and from the negative terminal of battery 9 to distal electrode 4b through lead wire 6b, copper pad 11b, and shaft 7b, respectively. As discussed in more detail below, when hypodermic needle syringe 15 is inserted through opening 16 and needle 17 contacts both proximal electrode 4a and distal electrode 4b, a complete electric circuit is created defined by battery 9, lead wire 6a, copper pad 11a, shaft 7a, proximal electrode 4a, needle 17, distal electrode 4b, shaft 7b, copper pad 11b, lead wire 6b, back to battery 9. An access door may be located on housing 3 to allow access to battery 9. Likewise, the unit 20 can include an inboard battery charging means (not shown) or be connected to an external battery charging means, as known in the art. Likewise, if the power supply is a transformer from alternating current to direct current, the unit 20 will be supplied with a power cord (not shown).

Stop 5a is mounted to deflector insulator 2 and prevents proximal electrode 4a from moving downwardly more than a set distance along shaft 7a. Similarly, stop 5b is mounted on first ceramic support substrate 1 and prevents distal electrode 4b from moving more than a set distance upwardly along shaft 7b. Stops 5 also may include switches such that when proximal electrode 4a contacts stop 5a, power through the circuit is interrupted. Such switches are known in the art. Stops 5 also nudge the electrodes 4 when contacted, thus assisting in rotating electrodes 4 during each use. By rotating the electrodes 4, the electrodes will last longer.

Figure 3:
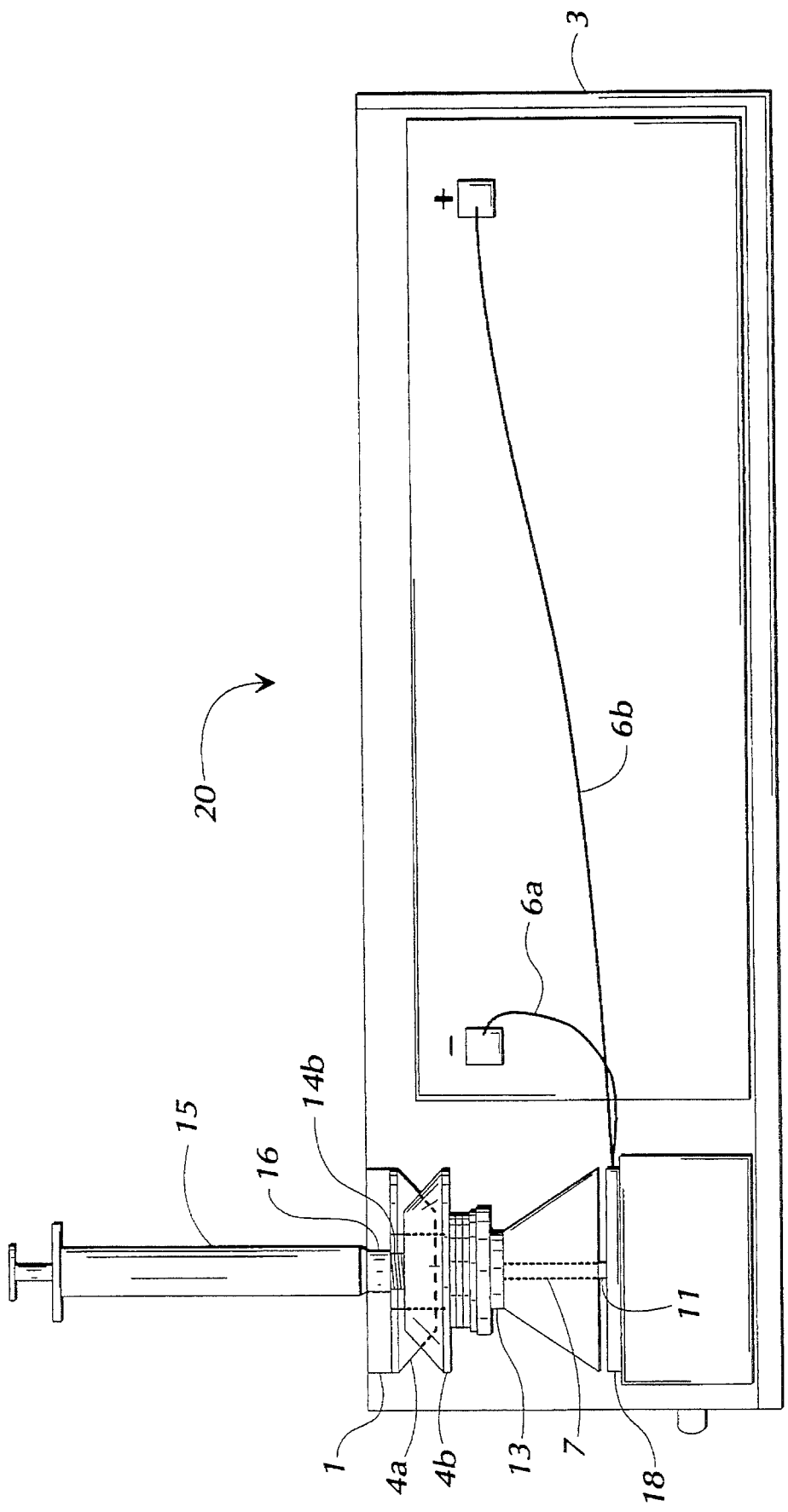
FIG. 3 is a side view, partly in section, of the needle destroyer unit as in FIG. 1 showing a hypodermic needle with the metal needle portion inserted into the burner unit.

FIG. 3 also contains a representation of the electrical wiring diagram for this embodiment of the needle destroyer unit 20. The needle destroyer unit 20 preferably is operated by a battery 9, typically a 12-volt battery or two 6-volt batteries. The battery 9 may be recharged using a recharging means (not shown) which is plugged into a conventional 110-volt alternating current wall socket. The preferred current source is a rechargeable battery 9, or rechargeable batteries, capable of delivering up to 12-volts served by a low voltage DC battery charging source. Preferably, the needle destroyer unit 20 may include its own battery recharging means powered through an AC power cord. Various other power sources can be used and are known to one skilled in the power source art. Typically, currents ranging from 9 to 25 amperes at 3 to 6 volts, or up to 50 amperes at 12 volts, are adequate in most cases to incinerate hollow hypodermic metal needles of conventional size. The entire needle destroyer unit 20 is compact in size and self contained and easily can be placed in an inconspicuous area within any medical office.

Figure 2A:
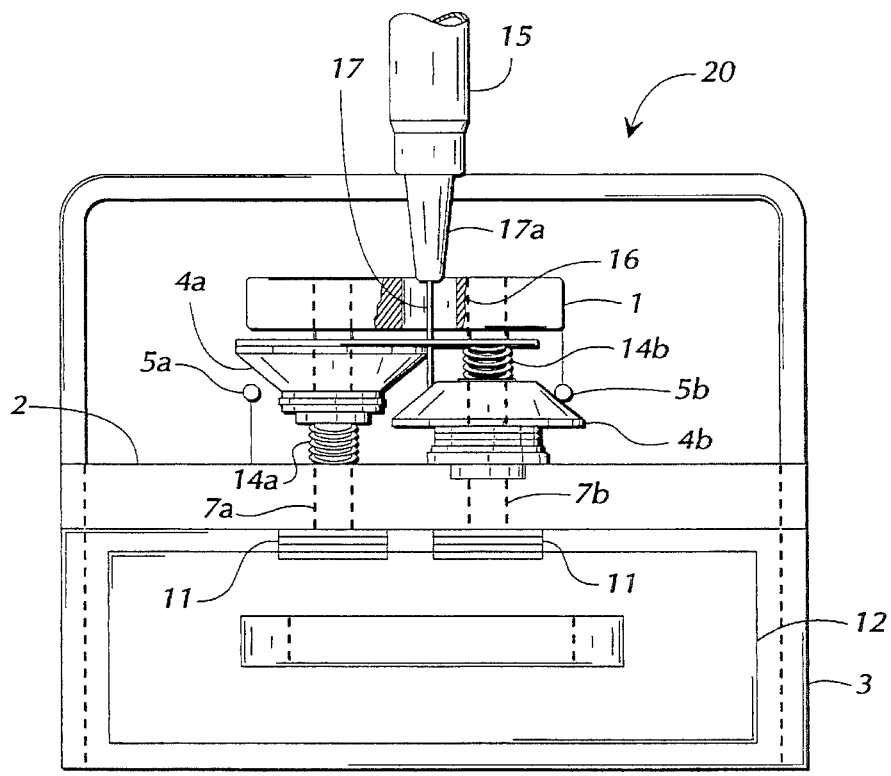
FIG. 2a is an end view, partly in section, of the needle destroyer unit as in FIG. 1 in its starting and operating position showing a hypodermic needle with the metal needle portion inserted into the burner unit.
Figure 2B:
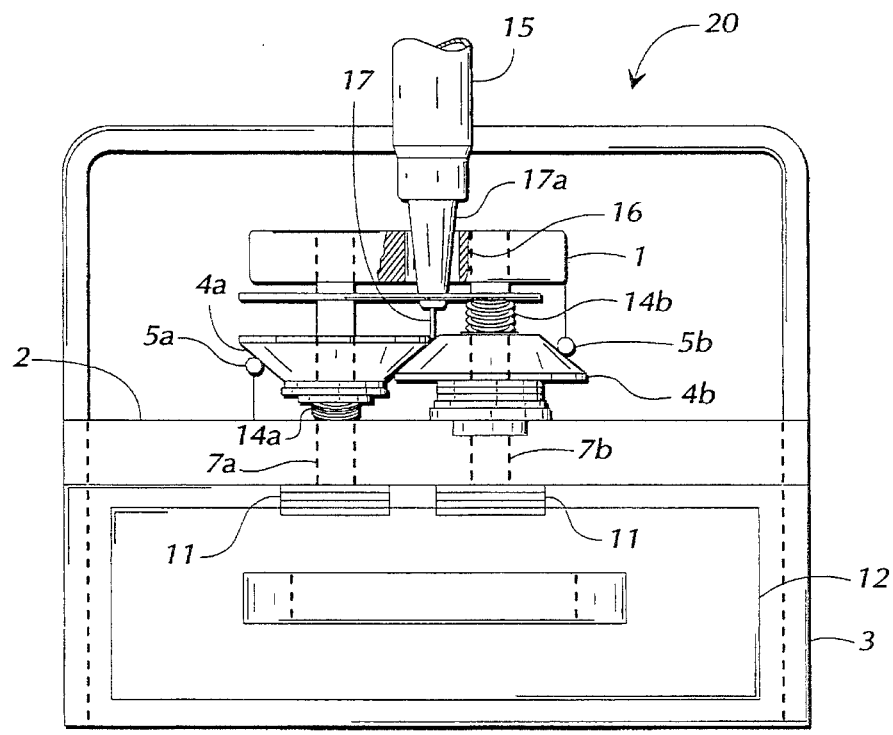
FIG. 2b is an end view, partly in section, of the needle destroyer unit as in FIG. 1 in its finishing position showing a hypodermic needle with the metal needle portion inserted into the burner unit.

With reference now in particular to FIGS. 2a and 2b, the sequence of operation of this embodiment of the syringe destroyer is described. A used hypodermic needle syringe 15 is inserted, needle 17 first, into opening 16. The shaft of needle 17 contacts proximal electrode 4 and, as the needle 17 is inserted further into the unit 20, the tip of needle 17 contacts distal electrode 4b, completing the electrical circuit. As electricity runs through the circuit, needle 17 is heated by electrical resistance heating sufficient to incinerate the needle 17 and to sterilize any needle ash or melted needle portions falling from the incinerating needle 17.

As the tip of needle 17 is continuously incinerated, the syringe 15 is continuously inserted further into the unit 20, thus allowing continuous incineration of the needle 17. Where the needle 17 is attached to the syringe 15 typically is a nub portion 17a. Because proximal electrode 4a and distal electrode 4b are separated by a set distance of up to one-half inch (½"), and preferably approximately one-eighth to three-sixteenths of an inch (⅛"–³⁄₁₆"), this length of needle 17 will remain when nub 17a contacts proximal electrode 4a. Because proximal electrode 4a is slidably mounted on shaft 7a and held in its upward position by compression spring 14a, when nub 17a contacts proximal electrode 4a, further downward pressure on the syringe 15 by the operator will cause proximal electrode 4a to slide downwardly on shaft 7a, compressing compression spring 14a. In this manner, proximal electrode 4a is forced downward and, therefore, closer to distal electrode 4b, thus shortening the gap between proximal electrode 4a and distal electrode 4b and allowing the incineration of the majority of the portion remaining of needle 17. Stop 5a prevents proximal electrode 4a from significant contact with distal electrode 4b so that neither electrode 4 is damaged by any such contact.

The ash created from the incineration of needle 17 falls downwardly by gravity onto deflector insulator 2. The lower surface of proximal electrode 4a and the upper surface of distal electrode 4b have downwardly tapering surfaces to allow any ash created by the incineration of the needle 17 to slide downwardly off of these surfaces onto deflector insulator 2. Likewise, any melted or other unincinerated portions of needle 17 will slide downwardly off of the electrode 4 surfaces onto deflector insulator 2. Such ash or other needle debris then will slide downwardly on the downwardly sloping upper surface of deflector insulator 2 into debris box 12. Debris box 12 can be removed from housing 3 at any time and the ash or other debris can be discarded.

The heat generated by the electrical circuit is sufficient to sterilize any ash or melted needle portion from needle 17. Therefore, the needle debris contained in debris box 12 is non-biohazardous and can be disposed of in any conventional manner. Likewise, the nub 17a and any other portion of needle 17 remaining on syringe 15 has been heated to a temperature high enough to sterilize. Therefore, the deneedled syringe 15 can be disposed of in any conventional manner.

Electrodes 4 may wear due to repeated usage. The electrodes 4 can be replaced by removing them from shafts 7 and substituting new electrodes 4. The relevant portions of the unit 20 are releasably secured to each other to allow such an exchange of electrodes 4, and other parts, if necessary. The electrodes 4 can spin freely on shafts 7 allowing electrodes 4 to turn with each use so that needle build-up or wear will not be in the same place on the electrodes 4 all of the time, which will greatly extend the electrode 4 life. Optionally, a small surfacer (not shown) may be included in the unit 20 to act upon the electrodes 4 to sweep off any build-up on the electrodes 4. Such a surfacer may be in the form of a brush, doctor blade, or any other surfacer which contacts the circumferential surfaces of the electrodes and the upper surface of distal electrode 4b. More than one surfacer may be used to allow greatest cleaning of the electrodes 4.

When the needle debris box 12 is full of needle refuse, for the most part ash, it can be removed from the housing 3. The needle refuse then can be disposed of in a correct manner. The refuse contained in the needle debris box 12 comprises non-biohazardous ash and, possibly, melted needle portions, all of which have been sterilized by the electrical resistance heat, and can be disposed of as ordinary trash. The syringe barrels then should be disposed of in a proper manner such as in a sharps' container or other biohazardous material disposal means.

The advantages of having such a needle destroyer apparatus 20 are numerous. The vaporization of the majority of the metal needle 17 and the sterilization of the remaining needle nub reduces the chance of needle sticks (puncture wounds). Even if such a needle stick occurs after the syringe 15 has been removed from the unit 20, the nub is sterile and therefore would not pass infection to whomever is handling the syringe. All points of access from the ambient to the interior of the syringe destroyer unit 20 may be lined with thermal resistant material, minimizing the escape of heat from the unit to the ambient. Likewise, the units may be shielded against radio frequency interruption so that the unit will not be a problem around sensitive equipment in the medical setting. The use of heat as the sterilization source, rather than chemicals, creates a more environmentally friendly unit and eliminates the risk of handling hazardous chemicals. The interior surfaces of the walls of housing 3 also may be lined with electrically insulative material, to prevent short-circuiting and inadvertent shocking of the operator.

Figure 5:
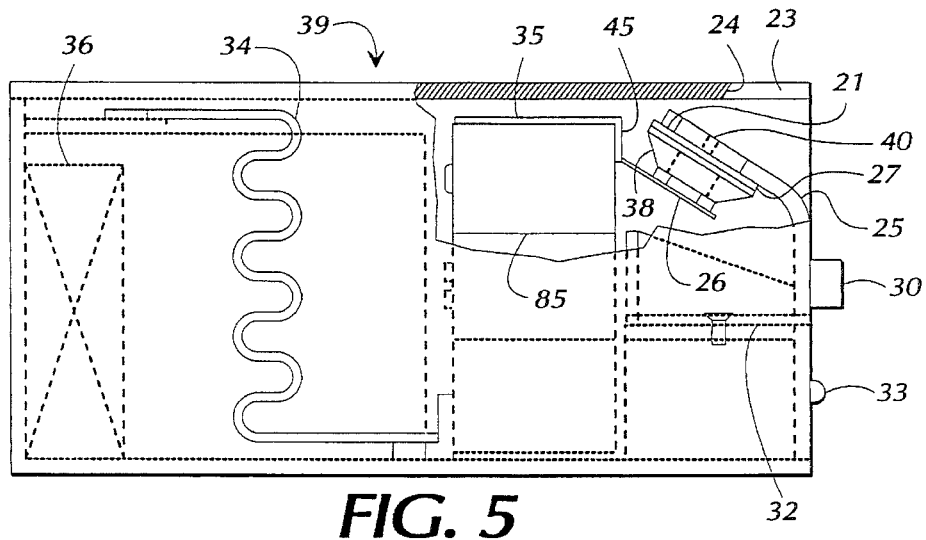
FIG. 5 is a side view of a preferred embodiment of the needle destroyer unit of the present invention.

FIG. 5 illustrates a side view of a preferred embodiment of the needle destruction unit of the present invention. The needle destruction unit 39 is contained in a housing 23 which, in a preferred embodiment, is approximately 7 inches in length, 3 inches in height, and 4 inches in width. The entire needle destruction unit 39 preferably weighs approximately 2½ pounds. The relatively small size of the needle destruction unit 39 facilitates handling and enhances the mobility of the needle destruction unit 39. Needle destruction unit 39 comprises an overlapping electrode arrangement which is essentially the same as the overlapping electrode arrangement shown in FIG. 1 and described above with the exception that the upper electrode is different in shape in the preferred embodiment of FIG. 5. The needle destroying means will be discussed in detail below with respect to FIGS. 5 through 13.

In the needle destruction unit 39 of FIG. 5 the needle portal entry 40 is recessed into the housing 23 and is disposed at an oblique angle to the surface of the housing 23. The needle portal entry 40 is through a door 25 which is rotatably mounted to the housing 23, as described in detail below with respect to FIGS. 10 through 11. The door 25 is provided with a handle 30 which is used to open the door 25 thereby allowing debris resulting from incineration to be removed from needle destruction unit 39. A portal entry plate 21, which is preferably comprised of stainless steel, is fastened to a fiberglass insulative plate 27 which is mounted to upper electrode 38. Electrode 38 is connected to a power source 85 via connecting assembly 26 and lead 35. The lower electrode is not shown in the side view of FIG. 5. The needle destruction unit 39 also comprises a filter module 34 and a fan 36. During incineration, fan 36 pulls air through filter module 34 to filter out any exhaust emission and pollutants generated during incineration.

Figure 12A:
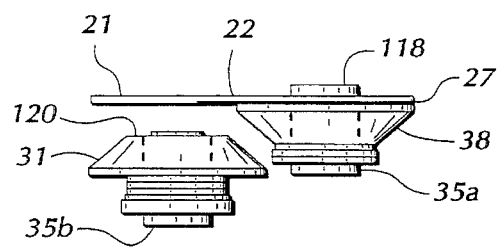
FIG. 12a is a top view of the electrodes of the needle destroyer unit of FIG. 5.
Figure 12B:
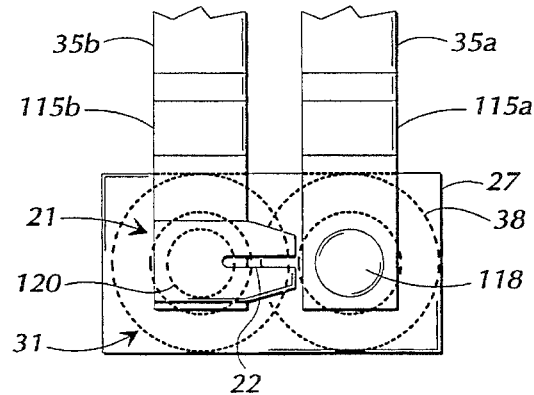

FIGS. 12a and 12b illustrate a top view and front view, respectively, of the overlapping electrode arrangement. The upper and lower electrodes 38 and 31, respectively, are indicated by the outer dashed circles in FIG. 12b. The entry plate 21 has a slit 22 formed therein and is fastened to a fiberglass plate 27. The needle destroying means is disposed below door 25, as shown in FIG. 5. During operation, a metal needle is inserted through opening 40 and slit 22 to form a resistive load between electrodes 31 and 38 whereby the current produced by power source 85 incinerates the metal needle. Any debris resulting from incineration is accumulated on fragment shelf 32. In order to remove the debris, door 25 is rotated in a upward direction and the needle destruction unit 39 is tipped forward to allow any debris to fall out of the needle destruction unit 39 into, for example, a sharps container.

Figure 6A:
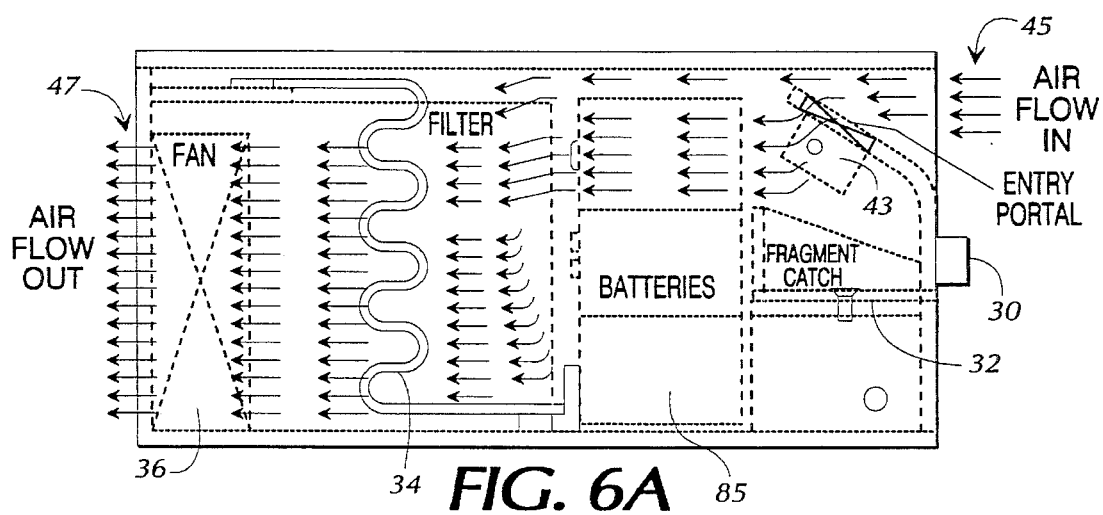
FIG. 6a is a side view, in schematic, of the needle destroyer unit of FIG. 5, showing air flow through the unit.
Figure 6B:
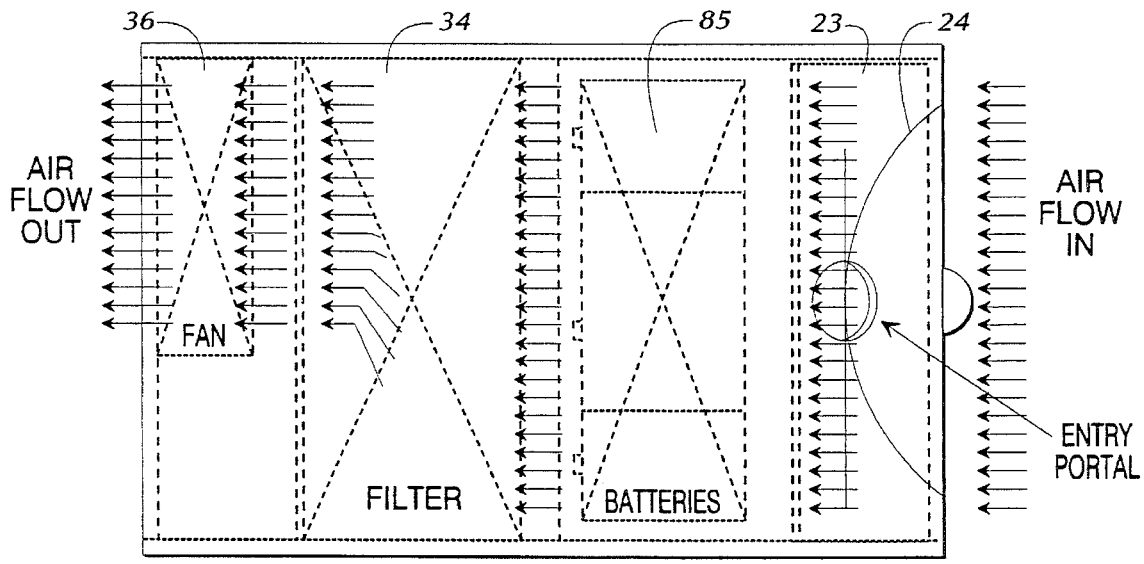
FIG. 6b is a top view, in schematic, of the needle destroyer unit of FIG. 5, showing air flow through the unit.

FIG. 6a illustrates a side view of the needle destruction unit of FIG. 5 showing the direction of air flow through the needle destruction unit as indicated by the arrows. The air flow through needle destruction unit 39 cools the unit and allows the air being pulled through the unit to be filtered. The needle destruction unit 39 is designed such that when fan 36 is turned on, a plenum is generated as the fan 36 pulls air through the needle destruction unit 39. A slit is located between the top of housing 23 and the top of door 25 to provide an air flow intake. When the fan 36 is turned on, a negative pressure is created within the interior of the needle destruction unit 39 causing air to flow into the needle destruction unit 39 as indicated by arrows 45. The air flows through the filter module 34 and is exhausted back into the room as indicated by arrows 47. The plenumed construction of the needle destruction unit 39 allows the air to be pulled sideways such that any exhaust emission from the high temperature heat used to burn the needle and any pollutants caused in burning the needle itself are trapped in filter module 34. As a result, odor free and particulate free air is exhausted back into the room, and air is not back exhausted through the front of the needle destruction unit 39. FIG. 6b illustrates a top view of the air flow through the needle destruction unit 39. The dashed line 24 shown in FIG. 5 (solid line 24 in FIG. 6b) indicates that the top of housing 23 is cut away to allow a needle to be inserted into portal entry 40.

Figure 7A:
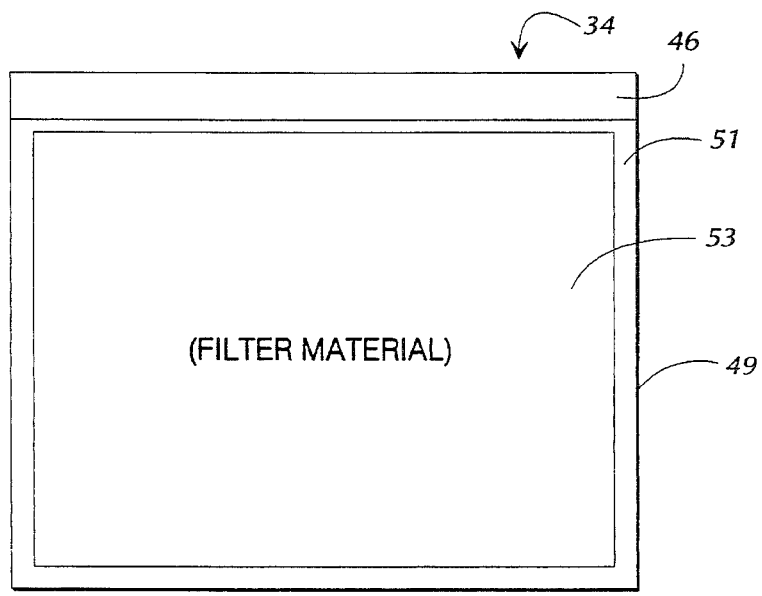
FIG. 7a is a front view of the filter module of the needle destroyer unit of FIG. 5.
Figure 7B:
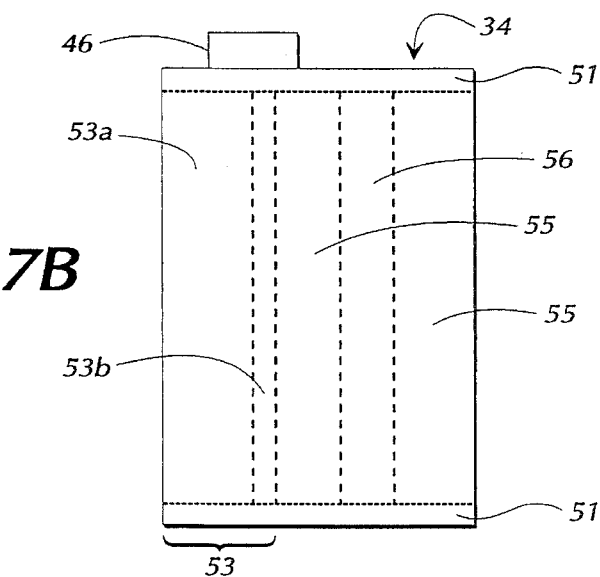
FIG. 7b is a side view of the filter module of the needle destroyer unit of FIG. 5.
Figure 7C:
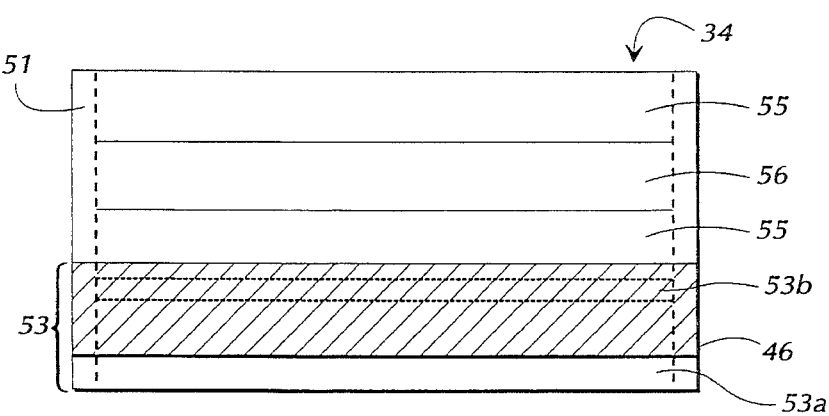
FIG. 7c is a top view of the filter module of the needle destroyer unit of FIG. 5.

FIGS. 7a through 7c illustrate several views of a preferred embodiment of the filter module 34 of the present invention. FIG. 7a shows a front view of filter module 34 relative to the direction of air flow. The filter module 34 is encompassed in a layer of sponge foam rubber 51 or the like which, in the preferred embodiment, is ⅛ inches thick. The sponge foam rubber layer 51 has adhesive on the inside and is connected at a foam joint 49. A separate piece of sponge foam rubber 46 having adhesive on its upper and lower surfaces is attached to the upper surface of sponge foam rubber layer 51. Separate sponge foam rubber piece 46 attaches the filter module 34 to the inside of needle destruction unit housing 23 to maintain filter module 34 in the position shown in FIG. 5. FIG. 7b illustrates a side view of filter module 34. FIG. 7c illustrates a top view of filter module 34.

The filter module 34 comprises a first filter 53 having a porous layer 53a for filtering out larger particles, such as soot from the incinerated needle and smoke particles, and a layer 53b which is saturated with antimicrobial disinfectant for killing bacteria, a second filter 55 which is comprised of activated carbon for filtering out gases and smoke, a third filter 56 which is comprised of potassium manganate for filtering out odors, and a fourth filter 55 which is also comprised of activated carbon for filtering out gases and smoke. Filters 55 are preferably 60% activated carbon. After filtering, the air exhausted back into the room is odor free and particulate free.

Although the preferred embodiment for the filter module 34 is as discussed above, it will be apparent to those skilled in the art that a variety of different types and arrangements of filters are suitable for use with the present invention. Moreover, the needle destruction unit 39 can be used without a filter module if so desired. However, for health reasons it is preferable to use a filtering means with needle destruction unit 39.

Figure 8:
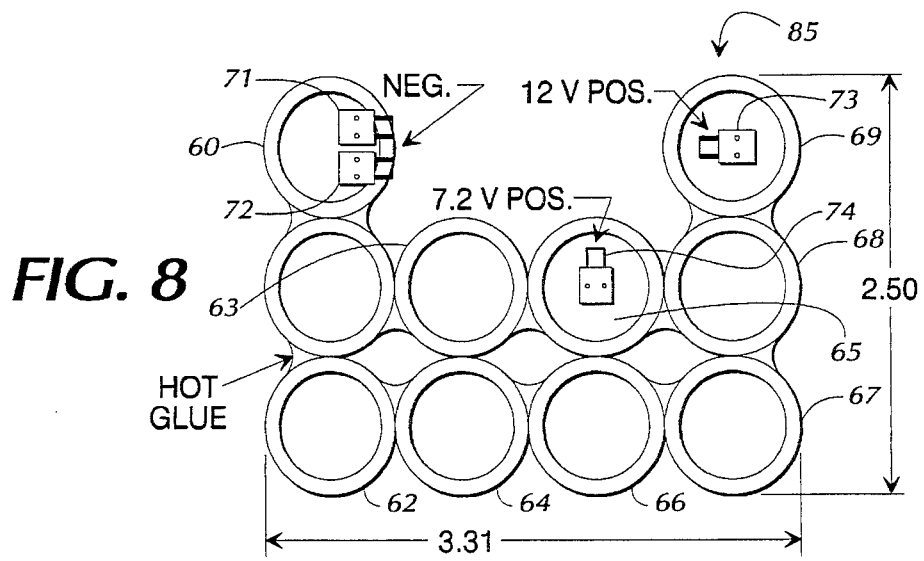
FIG. 8 is a back view of the preferred power source.

FIG. 8 illustrates a back view of a preferred embodiment of the power source 85 of the needle destruction unit 39. Power source 85 is preferably comprised of ten 1.2 volt ni-cad batteries. The batteries are connected in series to provide a total voltage of 12 volts. The needle destroying means requires only 7.2 volts to incinerate the needles. Therefore, the first six batteries of the series arrangement are tapped to provide 7.2 volts to the needle destroying means. All ten batteries of the series arrangement are tapped to provide 12 volts for operating the fan 36. Batteries 60 through 65 are tapped at terminals 71 and 74 to provide 7.2 volts to the needle destroying means. Tap 71 is connected by a lead to the lower electrode while tap 74 is connected by a lead to the upper electrode. The 12 volts needed to operate the fan 36 is provided by tapping the power source at leads 72 and 73.

Figure 9:
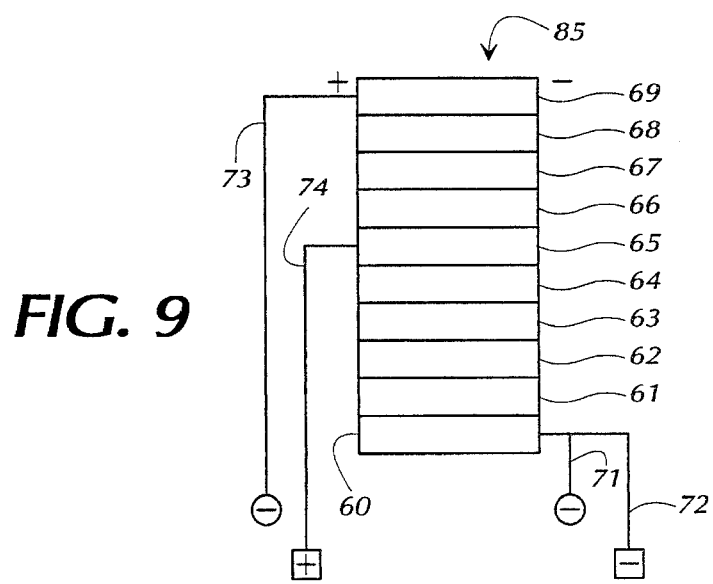
FIG. 9 is a schematic diagram of the preferred power source.

FIG. 9 illustrates a schematic diagram of the power source 85. The power source is recharged by using a standard 300 milliamp charger. Once the power source has been depleted, it can be recharged in four to six hours. Furthermore, the needle destruction unit 39 can be used while the power source is charging. After charging, the power source 85 contains enough amperage to effectively destroy up to approximately eighty needles, depending on the length and diameter of the needles being destroyed. Each time a needle is incinerated, the voltage level across terminals 71 and 74 drops slightly below 7.2 volts. When the fan 36 is turned on batteries 60 through 65 are slightly recharged by batteries 66 through 67, as discussed in more detail below with respect to FIG. 13. This allows more needles to be incinerated before recharging than would otherwise be possible.

Figure 13:
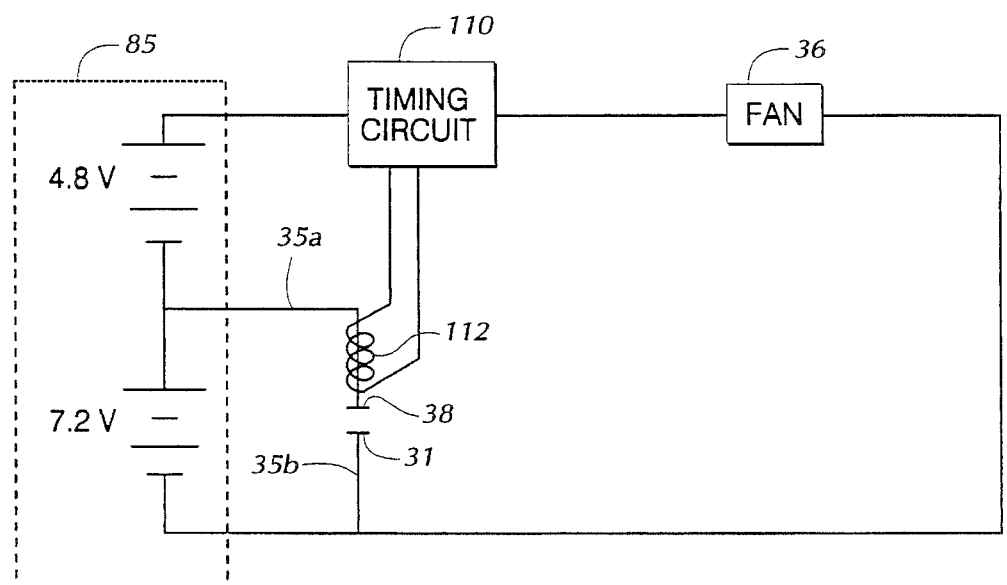
FIG. 13 is a circuit diagram of the power source connected to the electrodes, the switching means and the fan.

FIG. 13 illustrates a circuit diagram of the needle destruction unit 39. When a metal needle (not shown) is inserted between electrodes 31 and 38 a resistive load is created, thereby allowing current to flow through the portion of the circuit comprised of the 7.2 volt dc voltage source (i.e., batteries 60–65 in FIG. 8), lead 35a, electrodes 38 and 31, and lead 35b. As current flows through lead 35a, the magnetic flux generated by the current induces a current in coil 112 which is delivered to timing circuit 110. The timing circuit is preferably comprised of a 555 timer. When the current from coil 112 is delivered to timing circuit 110, a dc pulse of a preselected duration and of a magnitude sufficient to run fan 36 is delivered to fan 36. In a preferred embodiment, the duration of the pulse delivered to fan 36 is 7 seconds. However, as will be apparent to those skilled in the art, the timing circuit 110 can be adapted to turn fan 36 on for any preselected period of time.

Needle destruction unit 39 can incinerate a needle in approximately two seconds. The circuit shown in FIG. 13 is designed such that the fan remains on for approximately five seconds after a needle has been incinerated. This means that there is a period of time (i.e., approximately 5 seconds) during which no current flows across the electrodes 31 and 38 and the entire 12 volts of power source 85 supplies fan 36 by means of timing circuit 110. As current flows through this portion of the circuit, batteries 60 through 65, which constitute the 7.2 volt dc voltage source, are slightly recharged, thereby allowing more needles to be incinerated before recharging than would otherwise be possible.

Figure 10:
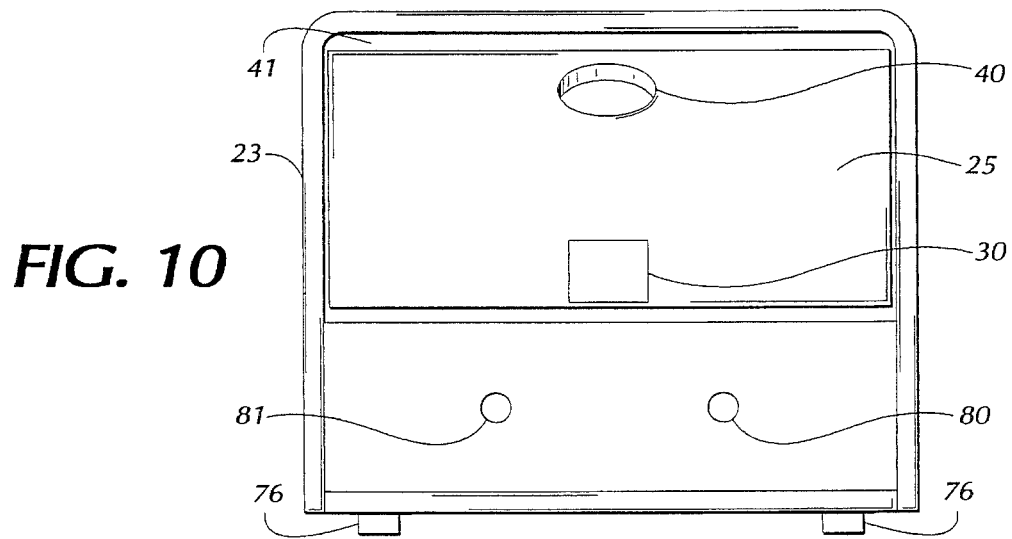
FIG. 10 is a front view of the needle destroyer unit of FIG. 5.

FIG. 10 illustrates a front view of the needle destruction unit 39. The slit opening between the door 25 and the top surface of the housing 23 is indicated by numeral 41. Door 25 has a handle 30 for rotating door 25 in the upward direction. LEDs 80 and 81 indicate when the fan is on and when the power source is being charged, respectively. Four rubber matting feet 76 are connected to the bottom side of housing 23.

Figure 11:
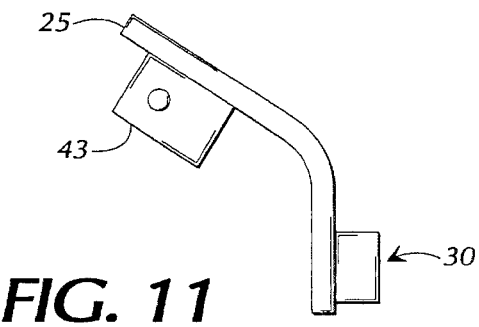
FIG. 11 is a side view of the door of the needle destroyer unit of FIG. 5.

FIG. 11 illustrates a side view of door 25. A pivot block 43 is integrally connected to each side of door 25 for rotatably mounting door 25 to housing 23. When an upward force is applied to handle 30 door 25 rotates upward on pivot blocks 43. Door 25 is mounted to housing 23 by the pivot blocks 43 which are attached to the housing 23 by a suitable fastening device such as a cotter pin.

The electrodes used in the preferred embodiment will now be described with reference to FIGS. 12a and 12b. FIG. 12a illustrates a top view of the overlapping electrode arrangement. The needle destroying means which comprises the overlapping electrode arrangement of FIG. 12a is essentially the same as that discussed above with respect to FIGS. 1 through 4 with the exception that the electrodes 31 and 38 are shaped differently in the preferred embodiment. The electrodes 31 and 38 are generally disc-like in structure having an upper surface and a lower surface parallel to each other, a circumferential surface, and a central, axial hole.

The upper surface of lower electrode 31 tapers downward and outward toward the lower surface of lower electrode 31 from the center toward the circumferential edge. The upper surface of upper electrode 38 and the lower surface of lower electrode 31 are flat. The lower surface of upper electrode 38 tapers upward and outward toward the upper surface of upper electrode 38 in the direction from the center of the upper electrode 38 toward the circumferential edge. Each of the electrodes 31 and 38 are rotatably mounted in such a manner that they can be moved from a fixed position at which they are not in contact to a position at which the electrodes abut each other. Electrodes 31 and 38 are rotatably connected to leads 35b and 35a by connecting means 86 and 26, respectively. Leads 35b and 35a are connected to negative and positive terminals of power source 85, respectively.

In accordance with the preferred embodiment, electrode 31 begins tapering at a radial distance of approximately 0.25 inches from the center of electrode 31. The upper electrode 38 begins tapering at a radial distance of approximately 0.50 inches from the center of electrode 38. In the preferred embodiment, the electrodes have the same thickness, approximately 0.20 inches, and are of the same diameter, approximately 1.00 inches.

The mounting assembly for mounting electrodes 31 and 38 will now be described with reference to FIG. 12b. FIG. 12b illustrates a front view of the needle destroying means. Electrode 38 is rotatably fastened by screw 118 to fiber glass plate 27. Electrode 38 is also rotatably fastened by a connecting means (not shown) to lead 35a. Lead 35a is attached to power source 85, as discussed above. Needle entry plate 21 is attached to fiber glass plate 27. Electrode 31 is rotatably attached to lead 35b by screw 120 and a connecting means (not shown). Any suitable connecting means (e.g., a nut-and-bolt assembly) can be used to attach the electrodes to their respective leads. The distance between the bottom surface of electrode 31 and the top surface of electrode 38 is approximately 0.50 inches when no force is applied to either of the electrodes. The needle destroying means is disposed below door 25 as shown in FIG. 5.

Leads 35a and 35b are resilient flexible strips of metal which function as springs which allow the electrodes to be forced into contact with each other while biasing the electrodes toward their home positions, which are as shown in FIG. 12a. Needle entry plate 21 has a slit 22 formed therein, underneath of which is a hole formed in fiberglass plate 27 to allow a needle to be inserted between electrodes 31 and 38. Leads 35a and 35b have upward bends 115a and 115b, respectively, formed therein. These upward bends, along with the resilience of the metal used to produce the leads, give the leads their spring-like characteristics.

By looking at the side view shown in FIG. 5, it can be seen that the portion of the lead which is connected to the electrode 38 is slanted downward. The bend 115 allows the electrode to be forced downward by exerting pressure on needle entry plate 21 through needle portal 40. As electrode 38 is forced into contact with electrode 31, electrode 31 is also forced downward. When the force exerted on needle entry plate 21 is removed, the electrodes are biased back to their home positions by their respective leads.

When a needle is inserted through needle portal 40 and slit 22 in between the electrodes, a resistive load is created which allows current to flow through the portion of the needle between the electrodes. As that portion of the needle is incinerated, the user simply continues pushing the needle forward until the entire needle has been incinerated. When almost all of the needle has been incinerated, the user presses the syringe into the needle entry plate which causes the electrodes and the electrodes to be pressed closer together whereby the needle shaft is incinerated up to the nub of the needle. When the user removes the syringe, the leads bias the electrodes back to their home positions, as shown in FIG. 18*a*.

Since the electrodes are axially and rotatably mounted, as discussed above with respect to FIG. 12*a*, the electrodes are allowed to rotate freely about their axes. This prevents the electrodes from being worn down because the same portion of the electrode will not be used each time a needle is incinerated. The typical friction occurring as a needle is inserted between the electrodes 31 and 38 causes some degree of rotation. Furthermore, since the electrodes 31 and 38 are preferably comprised of carbon, portions of the metal needle will not weld to the electrodes.

Although the mounting means discussed above with respect to FIG. 12*b* is the preferred mounting means for needle destruction unit 39, any mounting means which provides for movement as discussed above for incinerating needles is suitable for use with needle destruction unit 39. For example, the means for mounting the electrodes discussed above with respect to FIGS. 1 through 4 can be used to mount electrodes 31 and 38 in housing 23 for use with needle destruction unit 39. It will be apparent to those skilled in the art that many mounting arrangements are suitable for use with the present invention.

It will also be apparent to those skilled in the art that electrodes of a variety of different shapes and sizes can be used as part of needle destruction unit 39. Although the shapes and sizes of electrodes 31 and 38 as discussed with respect to FIGS. 14 through 16 are the preferred shapes and sizes of electrodes 31 and 38, the present invention is not limited to the electrodes shown in FIGS. 14 through 16. Similarly, although electrodes 31 and 38 are preferably comprised of carbon, the electrodes can be comprised of other materials as well.

The needle entry plate 21 picks up residual heat from the needle as it is melted which has the effect of sterilizing any biological life on the entry portal, thereby preventing contamination from being carried onto the next syringe. Due to the slit 22 in the needle entry plate 21, the act of positioning the syringe varies considerably depending on the placement of the user. Therefore, there is not a repetitive use pattern as is often associated with acquiring carpel tunnel syndrome. Also, the needle destruction unit 39 requires less than one pound of force to press a syringe into the unit to incinerate a needle.

Due to the low voltage used in the preferred embodiment to incinerate needles, there is no danger of sparks being thrown past the needle entry portal. Furthermore, by using a low voltage, there is no danger of the needle breaking which could lead to an aerosol release of blood. Also, the low current used by needle destruction unit 39 will not cause RF interference which makes it safe to use around hospital equipment.

In this manner, an apparatus for the destruction of syringe needles is provided. The present apparatus incinerates the metal needle portion of a hypodermic needle syringe, thus rendering the hypodermic needle syringe safe to handle and to dispose. The above-detailed description of the preferred embodiments is for illustrative purposes only and is not meant to limit the spirit and scope of the invention and its equivalents as defined in the appended claims.

What is claimed:

1. An apparatus for destroying metal needles having a shaft and a tip, said apparatus comprising:

a housing having an air intake opening, an exhaust opening and a needle entry portal formed therein;

first and second electrodes contained in said housing, said first and second electrodes mounted on mounting means a predetermined distance away from each other in an overlapping relationship to each other;

a fan contained in said housing, said fan disposed a predetermined distance away from said first and second electrodes;

a power source contained in said housing, said power source connected by a first conductive lead to said first electrode and by a second conductive lead to said second electrode to provide a voltage differential across said first and second electrodes;

a switching means contained in said housing, said switching means electrically coupled to said power source, to said fan, and to either of said first or second leads such that when a metal needle is inserted between said first and second electrodes, the metal needle forms a resistive load between said first and second electrodes which causes the metal needle to be incinerated and which causes said switching means to turn said fan on for a predetermined period of time, whereby said fan pulls smoke and emissions produced during incineration through said housing.

2. An apparatus for destroying metal needles according to claim 1 wherein said apparatus further comprises a filter module contained in said housing, said filter module disposed between said fan and said first and second electrodes such that, when said fan is on, said fan pulls the smoke and emissions through said filter module whereby the smoke and emissions are filtered out by said filter module.

3. An apparatus for destroying metal needles according to claim 2 wherein said filter module is comprised of a first filter having a porous layer and an antimicrobial layer, a second filter in contact with said first filter, said second filter comprised of activated carbon, a third filter in contact with said second filter, said third filter comprised of potassium manganate, and a fourth filter in contact with said third filter, said fourth filter comprised of activated carbon.

4. An apparatus for destroying metal needles according to claim 1 wherein said power source is a rechargeable 12 volt dc power source.

5. An apparatus for destroying metal needles according to claim 1 wherein said first and second electrodes are comprised of carbon.

6. An apparatus for destroying metal needles according to claim 2 wherein said air intake opening is a slit and wherein a plenum is created when said fan is turned on such that filtering by said filter module is facilitated.

7. An apparatus for destroying metal needles according to claim 1 wherein said apparatus further comprises a fragment shelf contained within said housing and disposed below said first and second electrodes for catching matter which falls from said first and second electrodes during incineration.

8. An apparatus for destroying metal needles according to claim 1 wherein said first and second electrodes are generally disc-shaped each having an upper surface, a lower surface and a circumferential surface.

9. An apparatus for destroying metal needles according to claim 1 wherein said first and second leads function as said mounting means for said first and second electrodes, respectively, and wherein said first and second leads are springs which maintain said first and second electrodes the predetermined distance away from each other in the overlapping relationship to each other unless a force is applied to said first or said second electrodes in which case the electrode having the force applied thereto will move such that the distance between said electrodes is less than the predetermined distance, and wherein the leads bias said electrodes in an effort to maintain said electrodes the predetermined distance away from each other in the overlapping relationship to each other such that when the force is removed, said leads substantially return said electrodes to the predetermined distance away from each other and the overlapping relationship to each other.

10. An apparatus for destroying metal needles according to claim 8 wherein the upper surface of said first electrode is of a first diameter and wherein the lower surface of said first electrode is of a second diameter wherein the second diameter is larger than the first diameter and wherein said first electrode tapers downward from the upper surface of said first electrode to the lower surface of said first electrode to form the circumferential surface of said first electrode, and wherein the upper surface of said second electrode is of a first diameter and wherein the lower surface of said second electrode is of a second diameter and wherein the first diameter of the upper surface of said second electrode is larger than the second diameter of the lower surface of said second electrode and wherein said second electrode tapers upward from the lower surface of said second electrode to the upper surface of said second electrode to form the circumferential surface of said second electrode.

11. An apparatus for destorying metal needles according to claim 10 wherein said first and second electrodes are comprised of carbon.

12. An apparatus for destroying metal needles according to claim 8 wherein the distance between said electrodes and the overlapping relationship of the electrodes is such that when a metal needle is inserted through the needle portal entry, the shaft of the needle contacts the circumferential surface of said first electrode and the tip of the needle contacts the upper surface of said second electrode, thereby creating the short circuit between said first and second electrodes.

* * * * *